(12) United States Patent
Cropper et al.

(10) Patent No.: US 9,452,077 B2
(45) Date of Patent: Sep. 27, 2016

(54) FOOT AND ANKLE ORTHOSES THAT ENABLE NATURAL MOVEMENT OF THE FOOT

(71) Applicants: Dean Cropper, Ashland, OR (US); Joseph T. Zachariasen, Talent, OR (US)

(72) Inventors: Dean Cropper, Ashland, OR (US); Joseph T. Zachariasen, Talent, OR (US)

(*) Notice: Subject to any disclaimer, the term of this patent is extended or adjusted under 35 U.S.C. 154(b) by 448 days.

(21) Appl. No.: 13/851,055

(22) Filed: Mar. 26, 2013

(65) Prior Publication Data
US 2013/0281898 A1  Oct. 24, 2013

Related U.S. Application Data

(60) Provisional application No. 61/615,879, filed on Mar. 26, 2012.

(51) Int. Cl.
*A61F 5/00* (2006.01)
*A61F 5/01* (2006.01)

(52) U.S. Cl.
CPC .................... *A61F 5/0127* (2013.01)

(58) Field of Classification Search
CPC ...... A61F 5/0127; A61F 5/00; A61F 5/0123; A61F 5/0113; A61F 5/0193; A61F 5/0585; A61F 13/00; A61F 13/061; A61F 13/066; A61F 13/065; A61F 13/14
USPC ................ 602/16, 23, 26–29, 60–62, 65, 66
See application file for complete search history.

(56) References Cited

U.S. PATENT DOCUMENTS

| 4,719,926 A | * | 1/1988 | Nelson ........................ 602/27 |
| 5,056,509 A | * | 10/1991 | Swearington ......... A61F 5/0127 36/89 |

(Continued)

FOREIGN PATENT DOCUMENTS

| DE | 44 04 911 A1 | 8/1995 |
| EP | 1 454 603 A1 | 9/2004 |

OTHER PUBLICATIONS

European Patent Office, "Supplementary European Search Report," mailed Jan. 7, 2015, in European patent application No. 13768134.2.

(Continued)

*Primary Examiner* — Kim M Lewis
(74) *Attorney, Agent, or Firm* — Durham, Jones & Pinegar, P.C. Intellectual Property Law Group (57) ABSTRACT

An ankle brace includes upper and lower members with a hinge therebetween. The hinge is configured to be positioned at a location that corresponds to, or at least approximately corresponds to, a true axis of rotation of an individual's foot relative to the tibia bone in his or her lower leg. That axis of rotation is located below the tibialtalor junction, along which tibia and talus articulate as the foot is moved between dorsiflexion and plantarflexion orientations. A foot orthosis includes an arch support that is configured to support at least a portion of a longitudinal arch of an individual's foot regardless of whether or not a ground reaction force is applied to the arch support or to the foot. Such an arch support and an orthosis of which it is a part may be configured to exert an upward force on the longitudinal arch regardless of whether or not any weight is applied to the foot or to the arch support. The arch support may be configured to follow or substantially follow a path of the posterior tibial tendon through the ankle and foot. An orthsis may include both the arch support and the hinge. Methods for support ankles and feet are also disclosed.

21 Claims, 8 Drawing Sheets

(56) References Cited

U.S. PATENT DOCUMENTS

| | | |
|---|---|---|
| 5,209,722 A | 5/1993 | Miklaus et al. |
| 5,445,603 A | 8/1995 | Wilkerson |
| 5,778,563 A | 7/1998 | Ahlbaumer |
| 5,902,259 A | 5/1999 | Wilkerson |
| 5,951,504 A * | 9/1999 | Iglesias et al. ............. 602/27 |
| 6,602,215 B1 | 8/2003 | Richie, Jr. |
| 8,968,228 B2 * | 3/2015 | Graddon et al. ............. 602/27 |
| 2002/0029009 A1 * | 3/2002 | Bowman ............. 602/27 |
| 2004/0236259 A1 | 11/2004 | Pressman et al. |
| 2005/0251073 A1 | 11/2005 | Roth |
| 2006/0084899 A1 * | 4/2006 | Verkade et al. ............. 602/27 |
| 2009/0216167 A1 * | 8/2009 | Harris ............. 602/27 |
| 2011/0021963 A1 | 1/2011 | Graddon et al. |
| 2011/0288461 A1 | 11/2011 | Arnold et al. |

OTHER PUBLICATIONS

United States Patent and Trademark Office, as the International Searching Authority, "International Search Report and Written Opinion," mailed Jun. 7, 2013, in related PCT application No. PCT/US2013/033942.

* cited by examiner

FOOT AND ANKLE ORTHOSES THAT ENABLE NATURAL MOVEMENT OF THE FOOT

CROSS-REFERENCE TO RELATED APPLICATION

A claim for priority is hereby made pursuant to 35 U.S.C. §119(e) to U.S. Provisional Patent Application No. 61/615,879, which was filed on Mar. 26, 2012 and is titled "FOOT AND/OR ANKLE SUPPORT SYSTEM AND METHOD" ("the '879 Provisional Application"). The entire disclosure of the '879 Provisional Application is, by this reference, incorporated herein.

TECHNICAL FIELD

This disclosure relates generally to apparatuses and methods for supporting feet and/or ankles and, more specifically, to apparatuses that support or stabilize one or more of an ankle, a medial column of a foot and an arch of a foot.

BACKGROUND OF THE INVENTION

A variety of braces, or orthoses, for feet and ankles are designed to apply force to a foot as the foot is forced against the ground under an individual's weight. This "ground reaction force," when applied against a foot orthosis and, in turn, by the foot orthosis to a foot, causes the foot to conform to the orthosis, and may provide the foot with some support.

The "Arizona" brace is configured to stabilize the ankle and, more specifically, to non-operatively correct posterior tibialis tendon dysfunction (PTTD), or flatfoot, which may occur as the posterior tibial tending (PTT) collapses or otherwise changes in a way that renders it unable to support the longitudinal arch of the foot. An Arizona brace is typically a form fitted leather brace that resembles a boot, and is configured to surround the lower leg, ankle, hindfoot and midfoot. Although Arizona braces are effective, they are also typically stiff and uncomfortable; they preclude proper dorsiflexion (at heel strike) and/or plantarflexion (at toe off). Any arch support provided by an Arizona brace is typically only provided as a ground reaction force during mid-gait. Arizona braces are also quite bulky, making it difficult to fit them into normal shoes.

Other braces, such as the "Richie" brace, may be less bulky than the Arizona brace, and may enable some movement of the foot about the ankle while addressing PTTD or other disorders. In particular, Richie braces and other similar ankle braces often include hinges with axes that are configured to be aligned (or approximately aligned) with only a portion of the tibialtalor junction, or talocrural joint—the site about which movement of the foot relative to the lower leg occurs. Unfortunately, the manner in which foot and leg sections of a Richie brace pivot relative to one another does not accurately mimic the manner in which an individual's foot pivots relative to his or her leg. Furthermore, because a Richie brace typically includes a stiff footplate, as with the Arizona brace, a Richie brace typically only provides a meaningful amount of ground force at mid-gait.

Off the shelf and custom molded orthotics, which are commonly referred to as "shoe inserts," only offer arch support when they have been inserted into shoes or other footwear. Even then, the primary arch support they provide is that resulting from ground reaction force as an individual walks.

A feature common to each of the foregoing orthoses is a somewhat stiff component that is configured to be placed under a majority of an individual's foot to provide arch support, via transfer of force from the ground, as the individual walks. The stiff materials transfer force from the ground and apply such force to the underside of the foot. Unfortunately, the stiff materials also impede flexibility and movement of the foot. They may also cause various foot muscles to atrophy. In some cases, in the absence of muscular activity, the foot may take on the shape of the orthosis. Instead of providing therapy or a solution to a foot or ankle disorder, orthoses that primarily provide arch support through ground reaction forces may actually exacerbate the problems and make the wearer ever more dependent on the orthosis.

Conventional soft bracing typically consists of flexible strapping, which allows the foot and ankle to move, but fails to provide adequate support for the medial column and/or the midfoot arch. Two reasons for this failure are (i) the limited amount of tension/force that can be applied with a flexible strap and (ii) the ease with which a soft brace collapses under a person's weight.

SUMMARY

An ankle brace may be configured to enable a foot to move about an ankle in a full range of motion between full dorsiflexion and full plantarflexion, while stabilizing the tibialtalor junction, or talocrural joint. In addition to an upper member that facilitates attachment of the braced to an individual's lower leg (also referred to herein as an "upper attachment member") and a lower member, such a brace may include a hinge that mimics the manner in which the tibialtalor junction enables to foot to move between dorsiflexion and plantar flexion. In various embodiments, the hinge may be configured to pivot about an axis of rotation that is configured to be positioned at a location below the tibialtalor junction. In more specific embodiments, the axis of rotation of the hinge may be positioned beneath an uppermost extent of a trochlear surface of the talus along which the tibia articulates, or the tibial trochlea of the talus. Even more specifically, the axis of rotation of the hinge of an ankle brace may be configured to be positioned coincident with, or at an approximate location of, an axis of an arc defined by the tibial trochlea of the talus. The axis of the arc defined by the tibial trochlea of the talus may be about an inch below the uppermost extent of the tibial trochlea of the talus. A hinge alignment feature may enable correct positioning of the hinge of an ankle brace as the ankle brace is secured in place over an individual's ankle. In some embodiments, the hinge alignment feature may be configured to receive a portion of the anatomy of the ankle (e.g., the medial malleolus, the lateral malleolus, etc.).

In various embodiments, additional stability in movement of the ankle may be provided by a tracking element. A tracking element may be configured to limit the arc in which the lower end of the tibia moves relative to the tibial trochlea of the talus as a foot travels between dorsiflexion and plantarflexion. In some embodiments, the tracking element may include an arcuate element (e.g., a receptacle, etc.) and a tracking guide that cooperates with the arcuate element. The tracking guide may be configured to remain in place relative to a predetermined part of a brace wearer's ankle (e.g., the tip of the medial malleolus, another portion of the medial malleolus, a portion of the lateral malleolus, etc.). The arcuate element may be configured for substantially alignment with the tibial trochlea of the talus. Such a configuration may enable an ankle brace to substantially limit movement of an ankle to normal motion of the ankle between dorsiflexion and plantarflexion. In addition, a tracking element of an ankle brace may be configured in a way that limits movement of the foot to a normal distance, or range of motion, between dorsiflexion and plantarflexion.

In a method of use, the hinge of such an ankle brace may be aligned with a location of the ankle located below the tibial trochlea of the talus. In some embodiments, location the hinge of an ankle brace may be aligned at a location about an inch below the tip of the medial malleolus. Proper alignment of the hinge may be facilitated by a hinge alignment feature on an inner surface of an upper member (e.g., an attachment member, etc.) of an ankle brace. In embodiments where the hinge alignment feature is configured to receive a portion of the anatomy of the ankle (e.g., the medial malleolus, the lateral malleolus, etc.), positioning of the ankle brace may include receipt or engagement of that portion of the anatomy of the ankle by the hinge alignment feature.

In another aspect, the lower member of a foot orthosis may comprise an arch support, which may be configured to provide support to a longitudinal arch of a wearer's foot (e.g., a collapsed posterior tibial tendon (PTT), etc.), or unloading the medial column of the foot, as may be useful for treating a variety of conditions, such as flatfoot, or PTTD. In various embodiments, a foot orthosis may be configured to provide support to the longitudinal arch, or unload the medial column of the foot, without the requirement of a ground reaction force. Such an arch support and an orthosis of which it is a part may be configured to exert an upward force on the longitudinal arch regardless of whether or not any weight is applied to the foot or to the arch support. In a specific embodiment, the foot orthosis may include an arch support that is configured to extend downward over a medial portion of an individual's ankle, then extend beneath the foot, and at an angle to a location beneath at least a portion of the longitudinal arch of the individual's foot. In some embodiments, the arch support may be configured to follow at least a portion of the path of the posterior tibial tendon. Such an element may be rigid enough to provide the desired support to the longitudinal arch (or to at least a portion of the longitudinal arch), yet flexible enough to enable normal movement of the foot and the muscles and tendons at and adjacent to the longitudinal arch during movement of the foot (e.g., during walking, etc.), and have sufficient resiliency to enable the arch support to continue supporting the longitudinal arch as the arch support flexes and after it flexes.

Such an arch support may be combined with an embodiment of ankle brace that includes a hinge and/or tracking element of the type disclosed herein.

A method for supporting at least a portion of a longitudinal arch of an individual's foot includes use of an arch support that exerts an upward force on at least a portion of the longitudinal arch without requiring a ground reaction force. The arch support may be positioned in such a way that it extends along at least a portion of the length of the longitudinal arch. In some embodiments, the arch support may be positioned beneath a portion of the posterior tibial tendon that extends down the medial side of the ankle and under the foot to the bases of the heads of the second, third and fourth metatarsals. Positioning of the arch support may include inverting the foot (i.e., rotating the foot medially) and, with the foot in an inverted orientation, positioning the arch support against at least a portion of the longitudinal arch and securing the arch support in place (e.g., by securing an ankle brace or foot orthosis of which the arch support is a part to the lower leg of the individual, by securing a distal end of the arch support to the individual's foot, etc.). With the arch support in place, the foot may be returned to a normal orientation, in which the arch support exerts an upward force on at least a portion of the longitudinal arch, regardless of whether or not a ground reaction force is applied to the arch support or the foot.

Other aspects, as well as features and advantages of various aspects, of the disclosed subject matter will become apparent to those of ordinary skill in the art through consideration of the ensuing description, the accompanying claims and the appended drawings.

BRIEF DESCRIPTION OF THE DRAWINGS

In the accompanying drawings, which form a part of the specification and are to be read in conjunction therewith, and in which like reference numerals are used to indicate like parts in the various views:

FIG. 1A is a side skeletal view of a left foot in nearly maximum dorsiflexion; FIG. 1A shows the talus, tibia and calcaneus bones in cross section, and depicting upper and lower partial portions of a conventional pivoting ankle brace in broken lines;

DETAILED DESCRIPTION

In various embodiments, an ankle orthosis of this disclosure includes: an upper portion configured to be secured above the medial (tibial) malleolus and/or the lateral (fibular) malleolus; and a low-profile hinge, which may include a single axis or multiple axes, or another articulating attachment device(s) (e.g., a monolithic or single-piece articulation device, etc.). In some embodiments, an ankle orthosis may also include a semi-rigid, flexible, and/or rigid plate that is configured to fit under a longitudinal arch of the foot and that may be configured to supports the longitudinal arch and, thus, the mid-foot.

Any embodiment of any or all of the foregoing features may be provided together or alone.

Figure 1A:
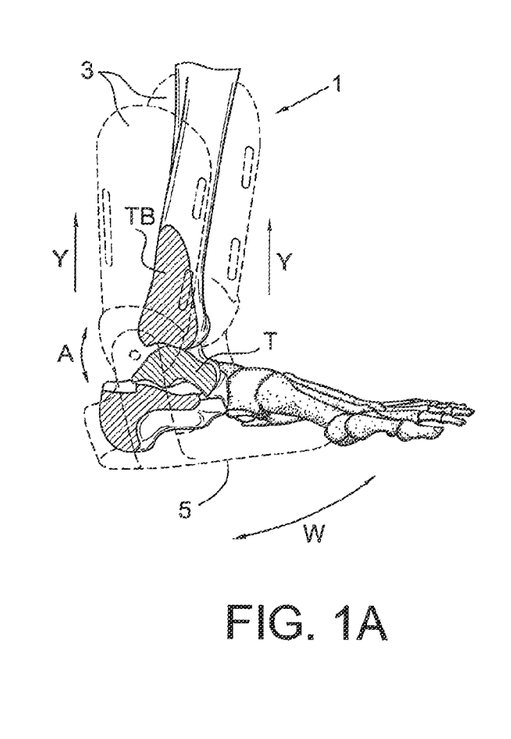
Figures 1B, 1C:
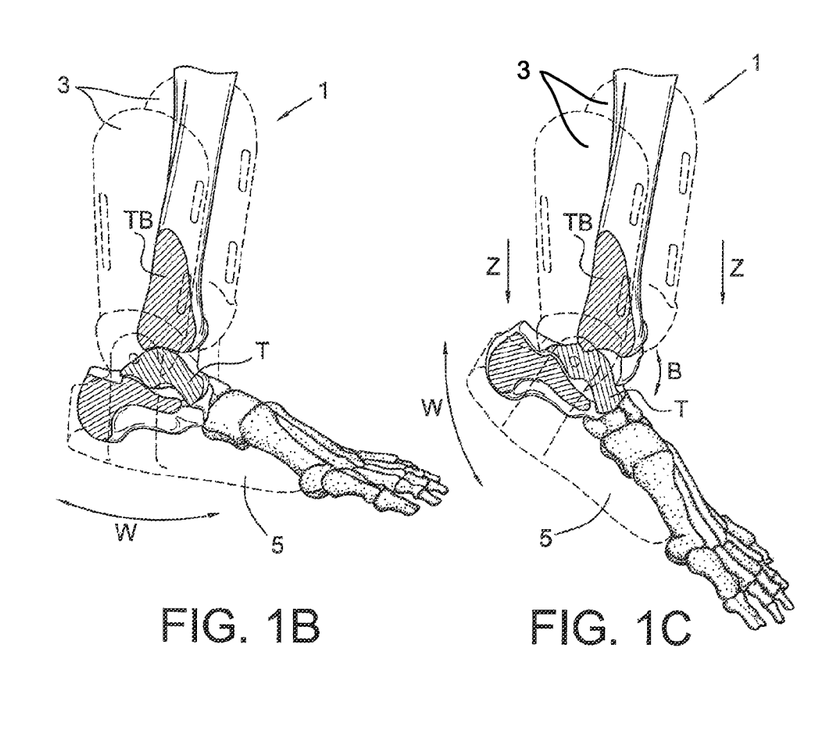
FIG. 1B provides a view of the left foot similar to that of FIG. 1A, with the foot positioned mid-way between maximum dorsiflexion and maximum plantarflexion.
FIG. 1C provides a view of the left foot similar to those shown in FIGS. 1A and 1B, but in a nearly maximum plantarflexion position.

FIGS. 1A-1C illustrate heretofor unrecognized and unexpected problems with several prior ankle braces including those disclosed by U.S. Pat. No. 6,602,215 to Richie ("the '215 Patent"), U.S. Pat. No. 5,209,722 to Miklaus ("the '722 Patent"), U.S. Pat. No. 5,902,259 to Wilkerson ("the '259 Patent") and U.S. Pat. No. 5,445,603 ("the '603 Patent"), such problems having been recently discovered through extensive research and evaluation. In particular, recent research and evaluation indicate that, as the foot moves about the ankle, the tibia follows a substantially arcuate path over the talus, with the actual axis or axes of rotation being located below the tibialtalor junction (or talocrural joint). The '215 Patent describes an ankle brace with one or more hinges that pivot about an axis located at or above (i.e., higher than) tibialtalor junction (or talocrural joint), or the lateral malleolus and the medial malleolus, throughout the entire range motion between dorsiflexion and plantarflexion.

These braces, such as shown in the partial rendering of a conventional ankle brace 1, such as a Richie brace, in FIGS. 1A-1C, require attachment above an ankle in a manner that places the axis of rotation of the conventional ankle brace 1 above (higher than) both malleoli and, thus, above the tibialtalor junction (or talocrural joint). As a result, during dorsiflexion and plantarflexion movements along directional arrows W, such placement destabilizes the tibialtalor junction (or talocrural joint) and loosens the support from its upper and lower attachment positions.

As seen in FIG. 1A, during plantarflexion, the conventional ankle brace 1, which is attached both below and above the tibialtalor junction (or talocrural joint), does not in fact pivot in conjunction with normal biomechanical movement, or true movement, of the ankle. Instead, the placement of the hinge of the conventional ankle brace 1 subjects the ankle to upward brace-pulling forces, represented by unidirectional arrows Y, thereby causing stress at the posterior interface between the talus T and tibia TB. This stress unnaturally pulls the tibia TB and talus T apart from one another at their posterior interface, as shown by bidirectional arrows A. Although natural joint stress is less severe at mid-gait, as seen in FIG. 1B, joint destabilization likewise occurs during plantarflexion. As seen in FIG. 1C, during plantarflexion the conventional ankle brace 1, which is attached both below and above the tibialtalor junction (or talocrural joint), does not pivot in conjunction with normal biomechanical movement of the ankle, thereby causing stress at the anterior interface between the talus T and tibia TB. This stress also unnaturally pulls the tibia TB and talus T apart from one another at their anterior interface, as show by bidirectional arrows B.

Moreover, during both dorsiflexion (FIG. 1A) and plantarflexion (FIG. 1C), misalignment between the axis about which the conventional ankle brace 1 pivots and normal biomechanical movement of the ankle consistently stresses the hinges of the conventional ankle brace 1, as well as the locations where the conventional ankle brace 1 attaches to an individual's leg and foot, which weakens the hinges and loosens the conventional ankle brace 1 at locations both above and below the ankle. More specifically, FIG. 1A shows that during dorsiflexion of the foot (with the toes upward and the heel downward along arrow W), the tibialtalor region (or talocrural joint) exerts a counter force against the conventional ankle brace 1, which pushes medial and lateral limb members 3 of the conventional ankle brace 1 upward, as represented by arrows Y. FIG. 1C shows that during plantarflexion of the foot (with the toes downward and the heel upward along arrow W), the tibialtalor region (or talocrural joint) exerts a counter force against conventional ankle brace 1, which pulls the medial and lateral limb members 3 downwardly, as represented by arrows Z. These upward (as shown by arrows Y in FIG. 1A) and downward (as shown by arrows Z in FIG. 1C) movements of the conventional ankle brace 1 loosen its upper portion from a wearer's leg. This repeated stress shifts the positioning of the conventional ankle brace 1, making it uncomfortable to wear, eliminating, or at the very least minimizing, its effectiveness in providing meaningful, consistent arch support throughout the full range of motion of the foot between dorsiflexion and plantarflexion (except to the extent that an upwardly directed ground reaction force might possibly effectuate such supportive function of such support, which occurs only during mid-gait ground strike, as illustrated in FIG. 1B) and eventually destroying the structural integrity of the conventional ankle brace 1.

Therefore, from one extreme of dorsiflexion to the other extreme of plantarflexion, conventional ankle braces like the Richie brace do not move coincident with the natural biomechanical movement of an ankle. Furthermore, conventional ankle braces 1 are not designed to account for any variance in the actual axes of rotation from one position along the motion continuum between plantarflexion and dorsiflexion in any one individual, or for variations from person to person.

Extensive research has also shown that not even ground reaction forces applied by a conventional ankle brace 1 during mid-gait will provide optimal or even adequate medial column lift because the single, uninterrupted foot plate of the conventional ankle brace simultaneously covers both the ankle and mid-foot arch, thereby failing to isolate and separately support either the mid-foot arch or the heel.

Figure 2A:
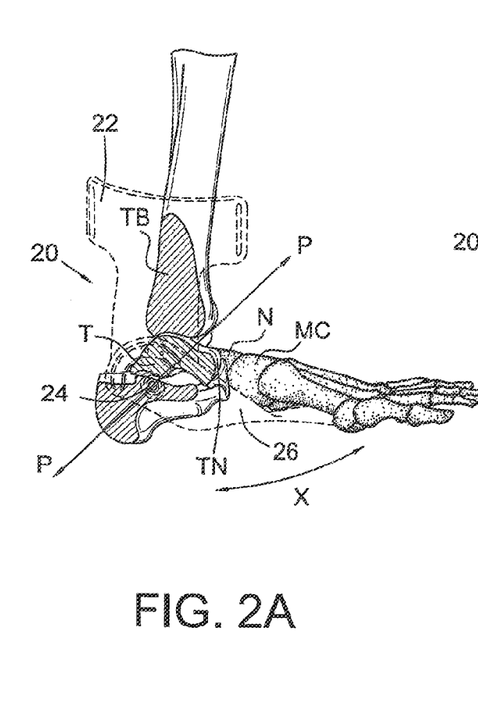
FIGS. 2A-2C depict the left foot in a manner similar to FIGS. 1A-1C, and in the orientations shown in FIGS. 1A-1C, respectively, but with an embodiment of ankle orthosis that pivots about an axis that is aligned with (or substantially aligned with) a true pivotal axis of an individual's ankle.
Figure 2B:
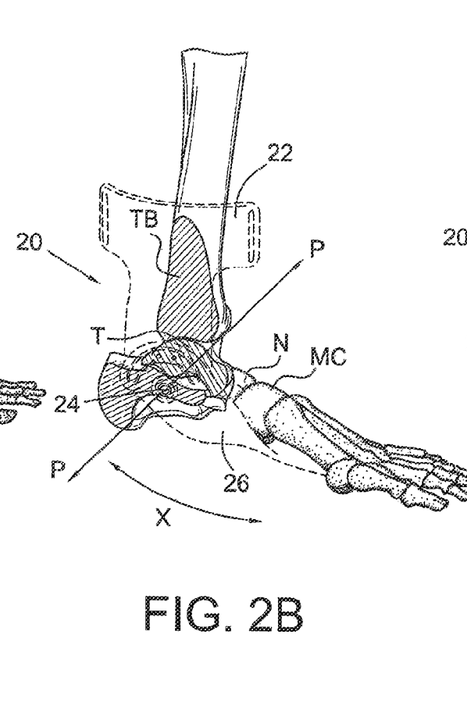
Figure 2C:
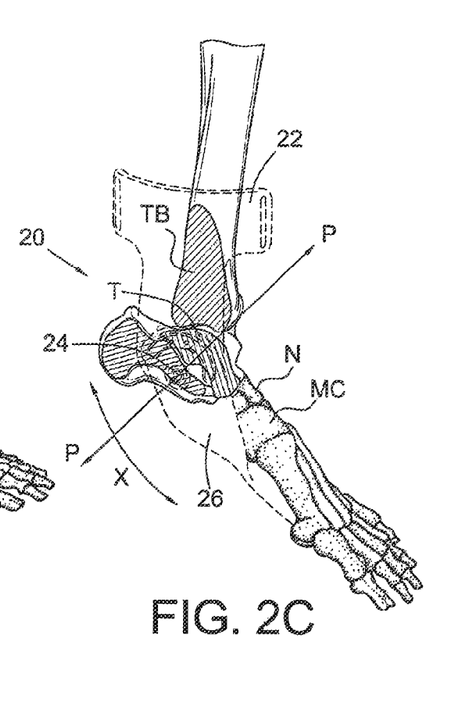

Referring to FIGS. 2A-C, in at least one embodiment, a brace 20 may be configured to stabilize and lift the medial column of a wearer's ankle and foot, reduce pronation of the midfoot, and reduce excessive valgus position in the subtalar joint. In the depicted embodiment, the brace 20 generally comprises an upper attachment member 22, a hinge 24, and a lower arch support 26. The upper attachment member 22 is configured to attach to a wearer's leg. The lower arch support 26 is configured to support a portion of a wearer's foot. The hinge 24 provides a pivoting interface between the upper attachment member 22 and the lower arch support 26.

The brace 20 is configured in such a way that the hinge 24 may be aligned (at least approximately aligned) with a true axis of rotation of the ankle (e.g., an approximate point about which the tibia pivots as it articulates over the talus, etc.). Extensive research has demonstrated that the most effective position of the hinge 24 and its axis of rotation P is not superimposed upon either malleolus, both of which are generally understood to be intersected by an axis of rotation through the tibialtalor junction (or talocrural joint) during normal dorsiflexion, but below the tibialtalor junction (or talocrural joint).

FIGS. 5A-5D and 6 illustrate a specific, but non-limiting, embodiment of a portion a brace 20 that includes a hinge 24 configured for alignment with a true axis of rotation of an ankle. Of course, each feature of the brace 20 may be varied according to various functional needs, such as the degree of support needed or desired, progression of treatment, and the like.

Figure 3A:
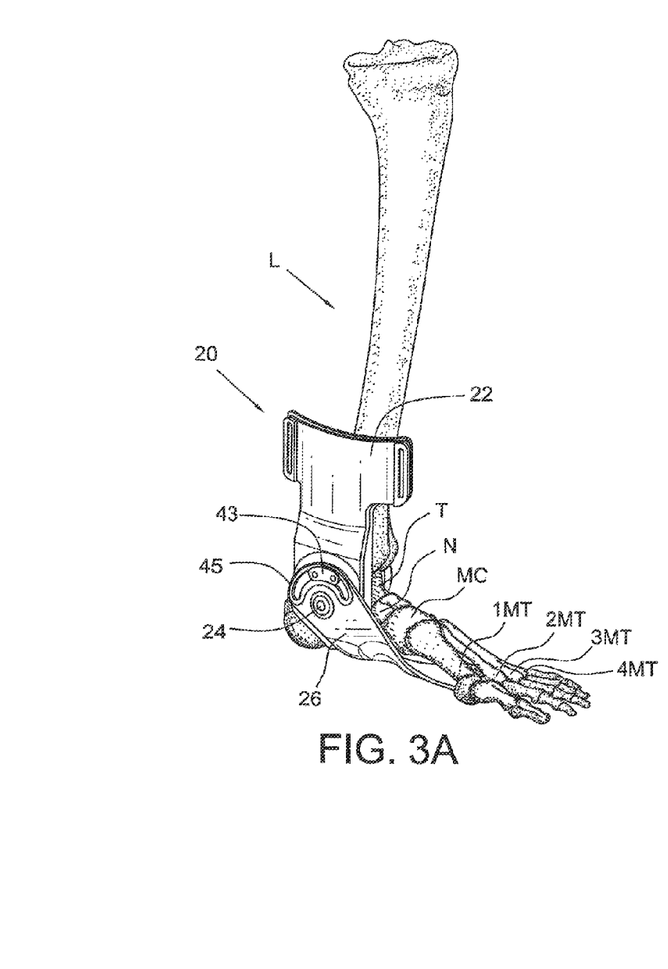
FIG. 3A is a perspective medial side view of the left foot and the embodiment of ankle orthosis shown in FIGS. 2A-C.
Figure 3B:
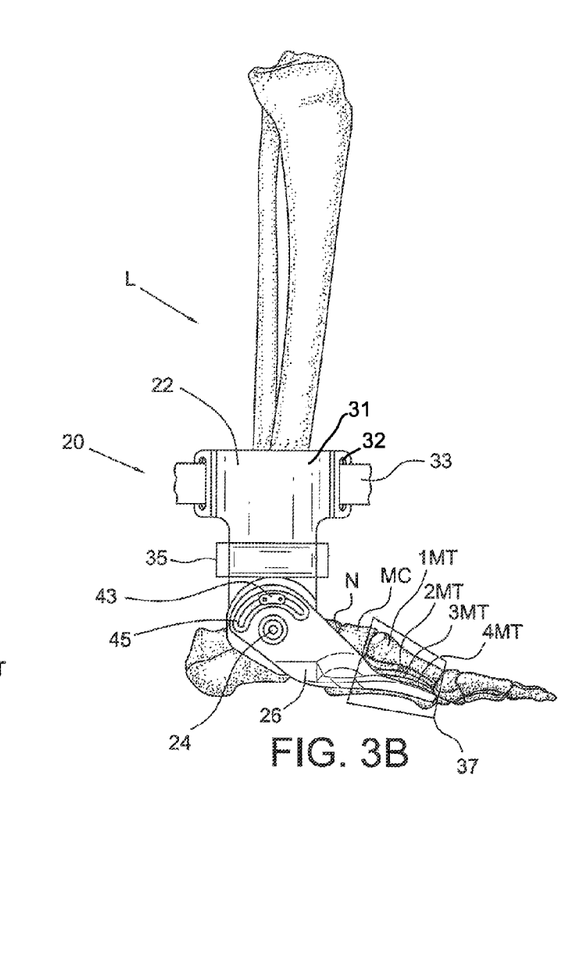
FIG. 3B is a medial side plan view of the left foot and the embodiment of ankle orthosis shown in FIGS. 2A-2C and 3A.

In the illustrated embodiment, the upper attachment member 22 of the brace 20 comprises a T-shaped element. Each arm 31 of the T includes a vertically oriented slot 32. As shown in FIG. 3B, each vertically oriented slot may be configured to receive a strap 33.

An inner surface of the upper attachment member 22 of embodiment of brace 20 depicted by FIGS. 5A-5D and 6 includes one or more cushions 63, which may enable the upper attachment member 22 to be intimately and comfortably secured in place over a portion of an individual's lower leg.

Figure 5A:
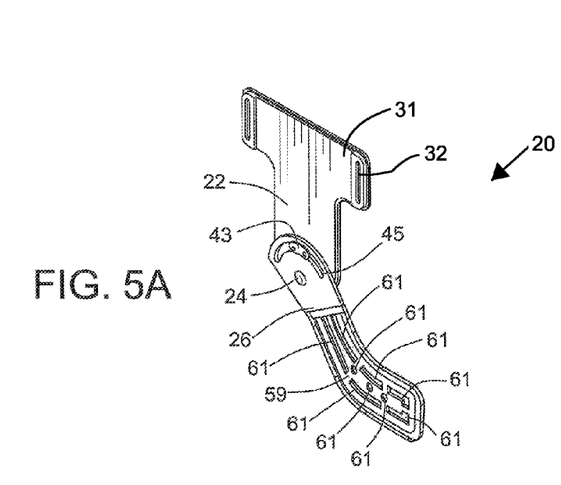
FIGS. 5A-5D are, respectively, outside perspective, inside perspective, outside plan and front plan views of a hinge of the embodiment of ankle orthosis shown in FIGS. 2A-2C, 3A and 3B.
Figure 5B:
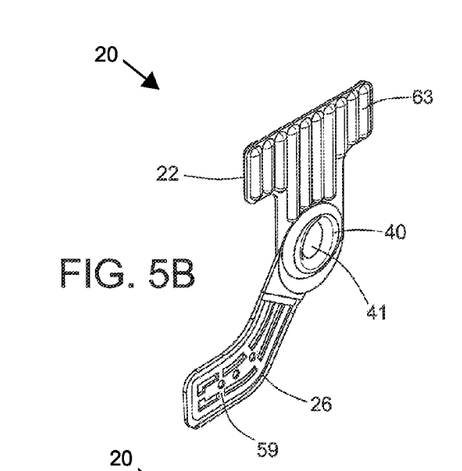
Figure 5C:
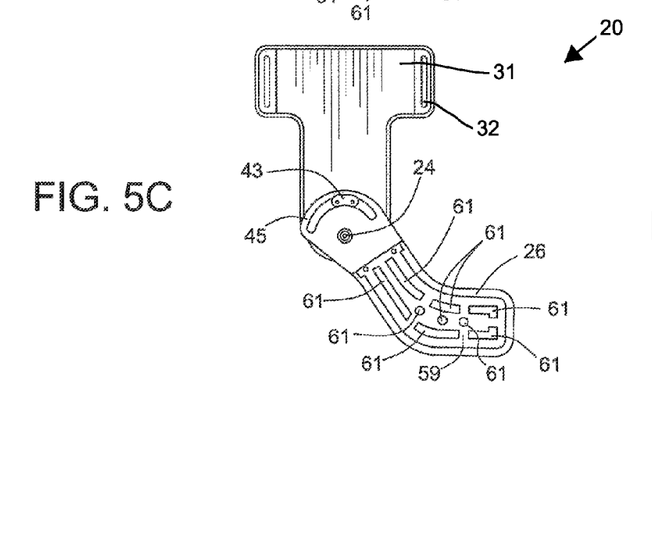
Figure 5D:
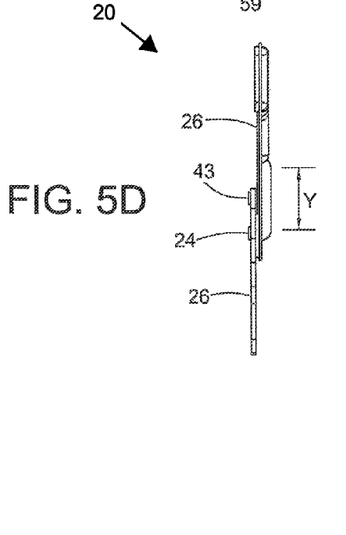

As FIGS. 5B and 5D show, an inner surface of the upper attachment member 22 of the brace 20 may include a hinge alignment feature 40. The hinge alignment feature 40 may be configured to guide a user in proper positioning of the brace 20 and, in particular, to ensure that the hinge 24 and its axis of rotation P are properly positioned. In some embodiments, the hinge alignment feature 40 may comprise a recess 41 configured to receive a malleolus on the side of an ankle (e.g., the medial malleolus, etc.) against which the inner surface of the upper attachment member 22 is positioned. Such a hinge alignment feature 40 may help hold the brace 20 in place as it is worn, and during movement of the foot with which it is used. The hinge alignment feature 40 may include a cushioning element (e.g., gel; a bladder filled with a compressible material; a structure including open cells or closed cells; etc.), which may enable the hinge alignment feature 40 to conform to the shape of the malleolus against which it is positioned.

On its outer surface, the upper attachment member 22 may include a tracking element, such as the tracking guide 43 shown in FIGS. 5A, 5C and 5D and the arcuate slot shown in FIGS. 5A and 5C. The tracking guide 43 may, as illustrated, protrude from the outer surface of the upper attachment member 22. In some embodiments, a position of the tracking guide 43 on the outer surface may be generally opposite from a location on the inner surface against which a malleolus is to be positioned; for example, within the range of arrow Y and within a similar range along the x-axis. In a specific embodiment, the tracking guide may be located directly opposite from a location on the inner surface against which the malleolus is to be positioned (e.g., opposite from a center of the hinge alignment feature 40, etc.). A configuration of the upper attachment member 22 and the manner in which the upper attachment member 22 is configured to be secured to an individual's lower leg, may hold the tracking guide 43 in a stationary (or substantially stationary) location relative to the ankle over which the brace 20 is worn.

As FIGS. 5A and 5C illustrate, when the upper attachment member 22 and the lower arch support 26 are assembled with one another (e.g., with the hinge 24, etc.), the tracking guide 43 may be configured to reside within an arcuate slot 45 in the lower arch support 26. The arcuate slot 45 may be configured in a way that will generally follow movement of the tibia (represented by leg L in FIG. 3A) over the talus T (FIG. 3A), or a profile of the tibial trochlea of the talus T (over which the tibia moves), when the brace 20 is properly positioned over an individual's ankle. In some embodiments, the length of the arcuate slot 45 may enable a full range of motion between full dorsiflexion and full plantarflexion. In some embodiments, the arcuate slot 45 may be configured to align with (or to be substantially aligned with) the tibialtalor junction (or talocrural joint) when the brace 20 is properly positioned over an individual's ankle. Thus, the tracking guide 43 and arcuate slot 45, as well as other embodiments of tracking elements that operate in a similar manner, may individually, or in conjunction with a properly positioned hinge 24, stabilize movement of the foot about the ankle (i.e., at any position between full dorsiflexion and full plantarflexion, etc.). In addition, a tracking element may be configured to limit the distance a foot may travel between dorsiflexion and plantarflexion (e.g., by way of the length of the arcuate slot 45, etc.).

The lower arch support 26 may be configured in a way that imparts it with a desired amount of rigidity, flexibility, and resiliency, and that enables the lower arch support 26 to provide a desired amount of support to the longitudinal arch of an individual's foot (e.g., unload the medial column, etc.). As a non-limiting example, the rigidity of a lower arch support 26 that is configured to support a foot during an advanced stage of a disorder (e.g., the third and/or fourth stages of posterior tibial tendon dysfunction (PTTD), or flatfoot, during which the posterior tibial tendon (PTT) and, thus, the longitudinal arch are beginning to collapse and the longitudinal arch begins to flatten; etc.) may exceed the rigidity of a lower arch support 26 that is configured for use with a less severe form of that disorder, or to address a different type of disorder.

In the embodiment shown in FIGS. 5A-5C, the lower arch support 26 includes an internal skeleton 59 defined by multiple elongated holes 61. The rigidity and flexibility of the lower arch support 26 may, of course, be tailored by adjusting the positions, arrangement and/or sizes of the holes 61.

The material(s) from which the lower arch support 26 (and the upper attachment member 22) is (are) formed may also at least partially dictate its rigidity and flexibility. The lower arch support 26 and the upper attachment member 22 may be formed from any material or combination of materials that will provide the desired rigidity and flexibility, strength, durability, fracture mechanics and any other desired characteristic(s). Without limitation, polypropylene, polyethylene and other plastics may be used. Optionally, one or more fillers (e.g., fibers, beads, microcapsules, etc.) may be used with the material(s) from which one or both of the upper attachment member 22 and the lower arch support 26 are formed.

In addition, in some embodiments, features that are formed from a relatively hard material may be coated with a softer, more compliant material (e.g., natural rubber, silicone, a compliant thermoplastic material (or oil-extended thermoplastic material), a cushioning material, etc.). In a specific embodiment, at least portions of the lower arch support 26 of a brace 20 may be covered with a compliant coating that has a hardness of about 40 Shore A to about 80 Shore A and, in even more specific embodiments, with a hardness of about 50 Shore A to about 70 Shore A.

Figure 6:
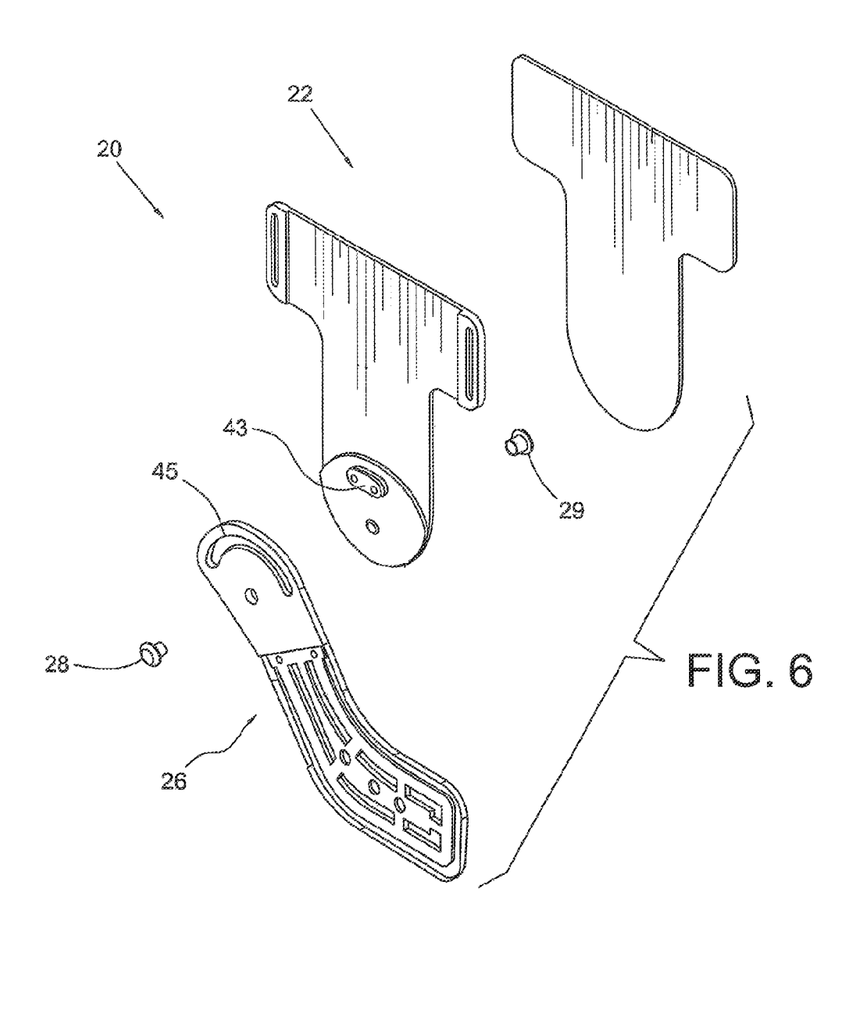
FIG. 6 is a perspective exploded view of embodiment of hinge shown in FIGS. 5A-5D.

The hinge 24 may be configured to secure the upper attachment member 22 and the lower arch support 26 to one another, as shown in FIG. 6. In that embodiment, the hinge 24 includes a pair of cooperating rivets 28 and 29 that are configured be disposed through aligned pivot holes in the upper attachment member 22 and the lower arch support 26. Each rivet 28, 29 includes an enlarge head; the heads of the rivets 28 and 29 being configured to hold the hinge 24 in place when the upper attachment member 22, the lower arch support 26 and the rivets 28 and 29 of the hinge are all assembled with one another. As an alternative to a hinge 24 with a single axis of rotation, a brace 20 may include an eccentric hinge, a hinge that is configured to pivot about a plurality of different axes, or any other hinge that will provide a desired type of movement of the upper attachment member 22 and the lower arch support 26 relative to one another.

In addition to the upper attachment member 22, the hinge 24 and the lower arch support 26 shown in FIGS. 5A-5D and 6, a brace 20 according to this disclosure may include features that secure the brace 24 to the leg and/or foot of an individual. These features may also be referred to herein individually or collectively as a "securing element." The securing element of a brace 20 may be configured to secure the brace 20 in place in a manner that maintains (or substantially maintains) a position of the hinge 24 and its axis of rotation P relative to a wearer's ankle.

FIG. 3B depicts a specific embodiment of a securing element, in which a group of flexible and, optionally, elastic and resilient straps 33, 35, 37 are configured to secure different parts of the brace 20 to the individual's lower leg L and foot. As shown in FIG. 3B, the vertically oriented slots of the illustrated embodiment of the upper attachment member 22 are configured to receive and retain portions of a strap 33. The strap 33 is configured to wrap around the lower leg L to hold an upper portion of the upper attachment member 22 in position on the lower leg L. In addition, the strap 33 may be configured to enable or accommodate arch lift throughout the entire range or motion of the foot between dorsiflexion and plantarflexion (e.g., the strap 33 may be elastic and resilient, etc.).

Another strap 35 of the depicted embodiment of securing element may be configured to wrap around the upper attachment member 22 at a location below the location of strap 33 but above the location of the hinge 24. The strap 35 may further secure the upper attachment member 22 in place on the lower leg L and, thus maintain (or substantially maintain) a position of the hinge 24 relative to the ankle (e.g., the location where it is positioned during medial column loading, etc., as the brace 20 is positioned and secured in place). The strap 35 may be secured in place in a manner that enables supination of the foot to an extent that is comfortable for the individual, or to an extent that enables the individual to move his or her foot without further damaging the ankle.

In addition, in the depicted embodiment, the securing element of the brace 20 includes a strap 37 that is positioned and configured to engage a forefoot. That strap 37 may urge the hinge alignment feature 40 laterally (i.e., toward the medial side of the ankle) in a manner that further enables the hinge alignment feature 40 to remain in a stationary (or a substantially stationary) position relative to the ankle over which the brace 20 is worn. Because of its position around the forefoot, the strap 37 may urge the lower arch support 26 into the longitudinal arch of the foot, which may lift the longitudinal arch and support the talonavicular joint. The strap 37 may provide such support even without a ground reaction force.

Of course, the securing element of a brace 20 may include other straps, additional straps, or even other features that enable the brace 20 to be secured in place, to support the ankle or foot in a desired manner, and to provide a desired amount of support at one or more locations.

The brace 20 may be attached to an individual's leg and foot in a manner that preloads the medial column of the foot. Such preloading may occur by positioning the hinge 24 correctly with respect to the ankle and/or foot. As an example, the lower arch support 26 of the brace 20 may be applied to the midfoot and secured in place relative to the midfoot (e.g., with strapping, etc.). The foot may then be inverted (i.e., rotated medially; e.g., to a supinated position; a normal foot will be slightly supinated during heel strike) as the hinge 24 is placed over the ankle, slightly below the malleolus. The upper attachment member 22 may then be secured to the lower leg. The upper attachment member 22 of the brace 20 may be secured to the lower leg in a manner that eliminates (or substantially eliminates) any slack between the lower arch support 26 and the upper attachment member 22.

Placement of the hinge 24 slightly below the malleolus may include positioning the hinge 24 below the malleolus a distance equal to about 25%, 30%, 40%, 50%, 60%, 70%, 80% or 90% of the distance between the top of the trochlea for the tibia (i.e., the articulating surface on the top of the talus) and the bottom of the calcaneus. In more specific embodiments, the axis of rotation P of the hinge 24 may be positioned about 60% to about 90% of the distance between the top of the trochlea for the tibia and the bottom of the calcaneus. In various embodiments, the hinge 24 may be positioned such that its axis of rotation P is located about a half an inch to about an inch below the malleolus.

In some embodiments, such as that depicted by FIG. 5B, the brace 20 (and, more specifically in the depicted embodiment, the upper support member 22), may be configured to position the axis of rotation P of the hinge 24 at an appropriate location. Without limitation, the brace 20 may include a hinge alignment feature 40, such as the illustrated depression, that may be configured to receive a portion of the medial malleolus (i.e., the bony protuberance on the medial side of each ankle).

Placing the hinge 24 so that its axis of rotation P is below the tibialtalor junction (or talocrural joint) may substantially decrease or eliminate brace-induced destabilization of the tibialtalor junction (or talocrural joint) throughout the full range of motion between dorsiflexion (FIG. 2A) and plantarflexion (FIG. 2C). Such placement of the hinge 24 may also decrease or eliminate loosening of the brace 20.

In embodiments where the hinge 24 is the only hinge of the brace 20 (e.g., in embodiments where the hinge 24 is not complemented by an opposing lateral hinge, etc.), the hinge 24 may also effectively provide a variable axis of rotation. Although the axis of rotation P of the hinge 24 is fixed, that axis of rotation P may, at any given point in time, coincide with variations in the true axis of rotation of the ankle, which may vary between dorsiflexion and plantarflexion as the tibia moves over the talus (at the tibialtalor junction, or talocrural joint).

By more accurately tracking normal motion of the ankle, the placement of the hinge 24 may stabilize the ankle while enabling motion between dorsiflexion and plantarflexion. In addition, proper placement of the hinge 24 may enable such movement without pushing or pulling on the upper attachment member 22 and, thus, without causing undesirable upward or downward movement of the upper attachment member 22 as an individual wearing the brace 20 walks or otherwise dorsiflexes or plantarflexes his or her foot.

Even further stability may be achieved by way of features that ensure that the tibia moves along (or substantially along) its intended, generally arcuate path over the talus. Embodiments of features that may provide such added stability include the tracking guide 43 and arcuate slot 45 described in reference to FIGS. 5A-5D, which are also shown in FIGS. 3A and 3B. Specifically, FIGS. 3A and 3B depict an arcuate slot 45 formed through the lower arch support 26 of the brace 20 and a tracking guide 43 that protrudes from the upper attachment member 22 of the brace, and that is configured to protrude through the arcuate slot 45. The arcuate slot 45 resembles and may be aligned with (or substantially aligned with) the path of the tibia (represented by leg L in FIG. 3A) over the talus T. In the illustrated embodiment, the tracking guide 43 is configured to remain in place over the malleolus (the medial malleolus in FIGS. 3A and 3B) and, because the tracking guide 43 is configured to reside within the arcuate slot 45, movement of the lower arch support 26 relative the upper attachment member 22 is limited to movement that occurs along the arcuate slot 45. These features and a variety of equivalent features enable the brace 20 to mimic normal movement of an ankle between dorsiflexion and plantarflexion.

In addition to supporting the tibialtalor junction (or talocrural joint) of the ankle during motion between plantarflexion and dorsiflexion, the hinge 24 may, in conjunction with upper attachment member 22 and lower arch support 26, function to provide a weight bearing platform through the medial column of the foot may be unloaded. In the depicted embodiment, the hinge 24 is configured to be positioned along and to press against the medial side of the foot and, thus, to stabilize the ankle against eversion-derived injuries or conditions. But the hinge 24 itself, as opposed to mere ground reaction forces during weight bearing moments of an individual's stride, provides consistent and effective unloading of a mid-foot arch throughout dorsiflexion and plantarflexion movements, via upward unloading of the mid-foot arch.

The hinge 24 may be configured to provide such support throughout the entire range of motion between dorsiflexion and plantarflexion, in part because of its axis of rotation P, which is below the tibialtalor junction (or talocrural joint), quite contrary to prior teaching.

Although the axis of rotation P of the hinge 24 may at times intersect the axis of rotation of the subtalar joint (which at least partially defines whether the foot is pronated or supinated), these axes are generally transverse, and not coincident, to one another. The axis of rotation P of the hinge 24 runs between the lateral and medial sides of the foot, whereas the axis of rotation of the subtalar joint generally runs from front to back. While the subtalar joint allows for inversion and eversion of the foot, it plays relatively little to no role in dorsiflexion or plantarflexion of the foot.

With continued reference to FIGS. 3A and 3B, the lower arch support 26 of the brace 20, which is attached to the upper attachment member 22 by the hinge 24, may provide a flexible orthotic device that is configured to fit under the foot. The lower arch support 26 of the brace 20 may comprise an elongated element that, in various embodiments, is configured to extend at an angle of about 110° to about 160° from the lower leg. The lower arch support 26 may have the same width and/or thickness or substantially the same width and/or thickness along most, at least about 60% to about 80% of its length, or along virtually all of its length. Each side of the lower arch support 26 may be equidistant from its central longitudinal axis for much or all of its length.

The lower arch support 26 may be configured to fit under at least a portion of the longitudinal arch of the foot. The lower arch support 26 may fit under all or part of the longitudinal arch without extending beneath or supporting the heel of the foot. The brace 20 may thus provide isolated, separate and independent support to the midfoot arch, along the full range of motion between dorsiflexion and plantarflexion. In specific embodiments, the lower arch support 26 may be configured to work dynamically with the foot to support the midfoot arch, by pulling the arch up rather than relying on a ground reaction force.

The lower arch support 26 may be configured to support the talonavicular joint between talus T and navicular bone N.

A central longitudinal axis of the lower arch support 26 may be configured to extend diagonally from the hinge 24, at its axis of rotation P (i.e., the point at which the axis of rotation P intersects the hinge 24) and wrap directly under the talonavicular joint. In some embodiments, the portion of the lower arch support 26 that wraps beneath the talonavicular joint may be oriented at an angle (e.g., about 45°; 20°, 25°, 30°, 35°, 40°, 45°, 50°, 55°, 60°, 65°, etc.) with respect to the ground when the individual is in a normal free-standing position.

In the embodiment depicted by FIGS. 3A and 3B, the lower arch support 26 of the brace 20 is configured to wrap at least partially along the sides of and under the talus T, navicular N and medial cuneiform MC bones, and then under one or more of the first metatarsal 1MT, second metatarsal 2MT, third metatarsal 3MT, and forth metatarsal 4MT. In the illustrated embodiment, the lower arch support 26 is configured to be positioned beneath all of the first through fourth metatarsals 1MT-4MT. The lower arch support 26 may also be configured to terminate, at the metatarsal head of one or more of the first, second, third, and fourth metatarsals 1MT-4MT.

In various embodiments, the lower arch support 26 may differ in configuration from the generally flat embodiment depicted by FIGS. 3A and 3B. The lower arch support 26 may be angled (e.g., dog-legged, L-shaped, etc.), curved, and/or include a tapered end. The lower arch support 26 may include features that impart it with a more rigid construction (e.g., elongated ribs, etc.). In some embodiments, the flexibility of the lower arch support 26 may vary along one or more of its length, width and thickness. Such variable flexibility can be achieved in a variety of ways; for example, by varying the thickness and/or width of the lower arch support 26, by using different materials (e.g., materials with different hardnesses, similar composites with different types of reinforcement (e.g., different fiber lengths, etc.), similar composites with different proportions, etc.) to form different parts of the lower arch support 26 (e.g., laminated layers (including embodiments where the layers in two or more sections differ, at least partially, from one another), interconnected sections, etc.).

A brace 20 may be configured in such a way that its lower arch support 26 can be removed and replaced. Such modularity may be useful for replacing a worn or damaged lower arch support 26, for tailoring the amount of arch support to be provided to a particular individual, for changing the amount of arch support provided to a particular individual over the progression of treatment, to accommodate different diagnoses, to accommodate different foot sizes, to accommodate changes in the conformation of an individual's foot (e.g., decreases or increases in size due to changes in swelling, etc.), to optimize comfort or for any other suitable reason.

In some embodiments, the lower arch support 26 contributes only a portion of the total arch support (or heel support) that may be provided by the brace 20. In such embodiments, the brace 20 may also comprise one or more other features that provide arch support.

Figure 4:
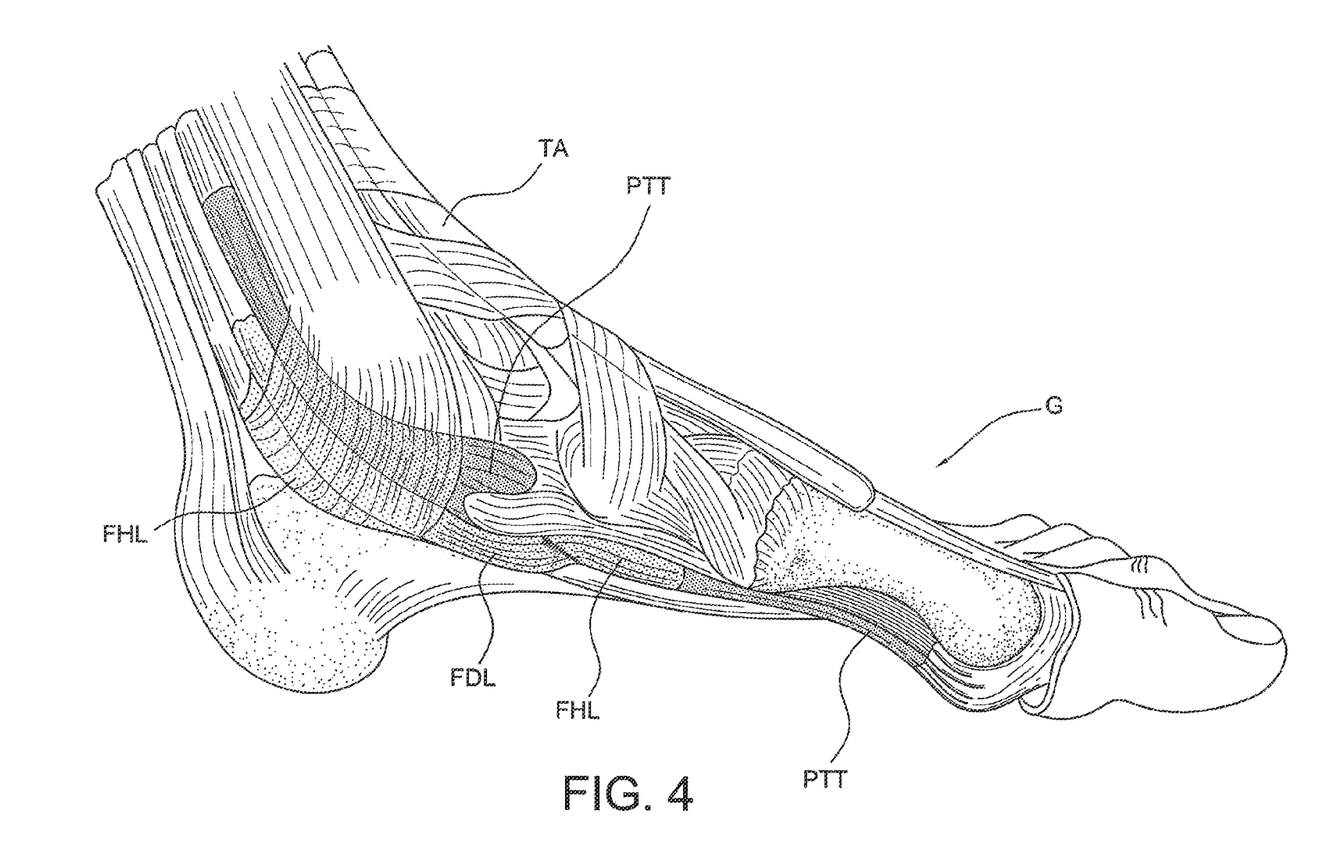
FIG. 4 is a partial cut-away view of the medial side of a left foot, showing the general positioning of various tendons of the foot with respect to its skeletal and muscular anatomy.

With continued reference to FIGS. 3A and 3B, and added reference to FIG. 4, the lower arch support 26 may be configured to work dynamically with the foot G to support the posterior tibial tendon PTT, which extends from behind the medial malleolus and the talus T (FIG. 3A) and a variety of locations, including the bases of the second, third and fourth metatarsals 2MT, 3MT and 4MT (FIGS. 3A and 3B), the tuberosity of the navicular N bone (FIGS. 3A and 3B) and the plantar surface of the medial cuneiform MC bone (FIGS. 3A and 3B). Several surrounding tendons include the anterior tibial tendon TA, the flexor hallucis longus tendon FHL, and the flexor digitus longus FDL.

The lower arch support 26 of the brace 20 may be configured to follow the general path of the posterior tibial tendon PTT tendon from the medial side of the ankle, under the navicular N bone and the medial cuneiform MC bone to the bases of the heads of the second, third, and fourth metatarsals 2MT, 3MT and 4MT. As a more specific, but non-limiting example, the lower arch support 26 may be configured to extend from a location beneath the distal end of the longitudinal arch of the foot (at about the end of the metatarsal joint heads), proximally under the foot G, then curve to extend along the medial side of the talonavicular joint. With this type of positioning, and sufficient flexibility and resiliency to accommodate the type of movement (e.g., to enable use of muscles and tendons of and adjacent to the longitudinal arch, etc.) that occurs in a normal, healthy longitudinal arch during walking, the lower arch support 26 of the brace 20 functions as a suspension device that supports the posterior tibial tendon PTT and, thus, cooperates with the normal dynamics of foot movement in a manner that coincides with and supplements such movement throughout the full dynamic range of motion between dorsiflexion and plantarflexion. In addition, the lower arch support 26 supports the longitudinal arch as the posterior tibial muscle, or tibialis posterior, cycles between eccentric and concentric contractions. Thus, the lower arch support 26 enables the foot G to respond to a variety of conditions, including, but not limited to, the ability to absorb varying loads and the ability to adapt to uneven surfaces. The dynamic range of flexible support provided by the lower arch support 26 of the brace 20 is unlike other bracing methodologies, which typically hold the foot in uniform position.

In a specific embodiment, the lower arch support 26 may have a width of about 1.36 inches (about 34 mm) to about 1.52 inches (about 39 mm), which may enable the lower arch support 26 to control the talonavicular joint without unduly affecting the first metatarsal ray; i.e., without causing the halux to unduly lift from the ground.

Turning now to FIGS. 7A-7E, another embodiment of a brace 50 is depicted and described. That brace 50 is configured to provide heel support (e.g., subtalar support, etc.) via lower support member 52. The lower support member 52 may be configured to support various portions of the hindfoot, such as the talonavicular joint (between the talus T and navicular N bones), as well as the medial cuneiform MC, intermediate cuneiform IC, lateral cuneiform LC and cuboid C bones. In some embodiments, such as that shown by FIGS. 7A-7E, the lower support member 52, may be configured so that it will not extend beneath or otherwise support the longitudinal arch of the foot.

The brace 50 also includes medial and lateral members, which extend upwardly from opposite sides of the lower support member 52. Each of the medial and lateral members of the brace 50 includes a hinge 58, 59. As FIGS. 7B and 7C illustrate, the axes of rotation P and O of hinges 58 and 59, respectively, or the points about which the hinges 58 and 59 pivot, are or coaxial, or aligned. FIGS. 7C and 7E demonstrate that the axes of rotation P and O may pass through the bottom portion of the talus T, or just under the bottom of the talus T.

Figure 7A:
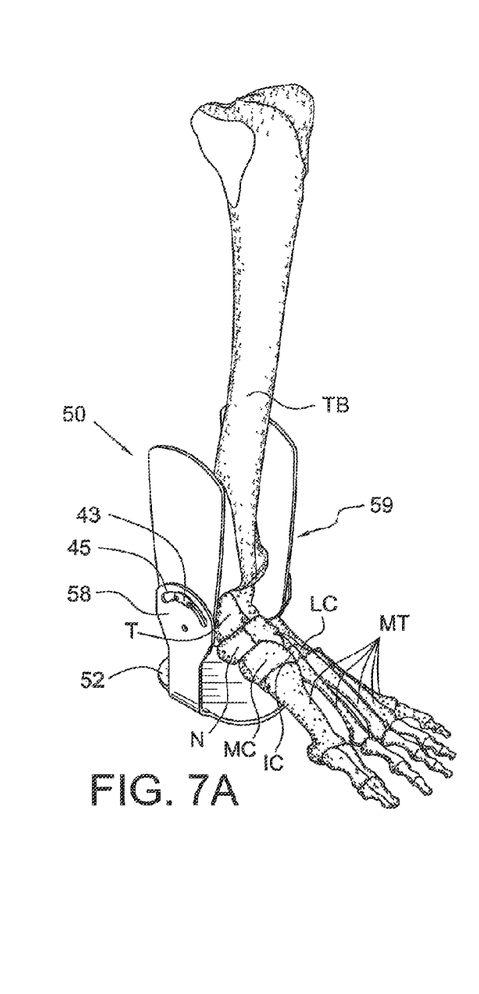
FIGS. 7A-7D are, respectively, a medial side perspective view, a medial side plan view, a cross-sectional view (taken from the rear, along line 7C-7C of FIG. 7B) and a front plan view of another embodiment of an ankle orthosis that is configured to pivot about an axis that is aligned with (or substantially aligned with) a true axis of an ankle.
Figure 7B:
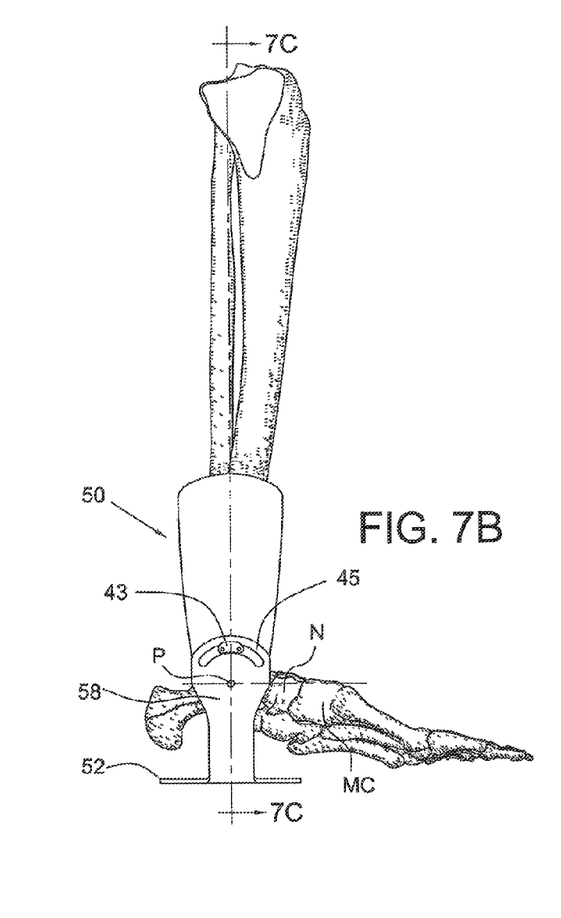
Figure 7C:
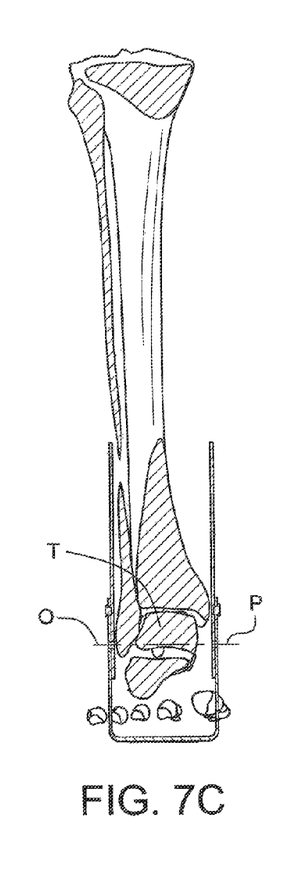
Figure 7D:
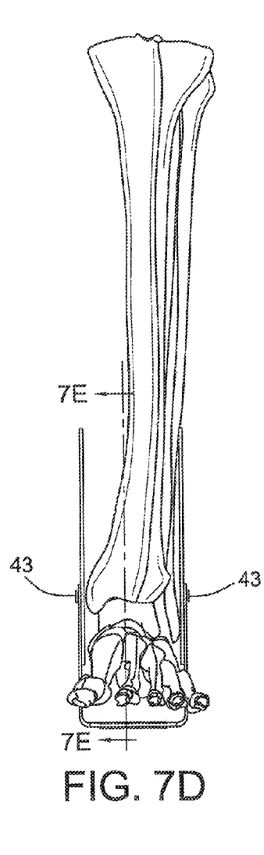
Figure 7E:
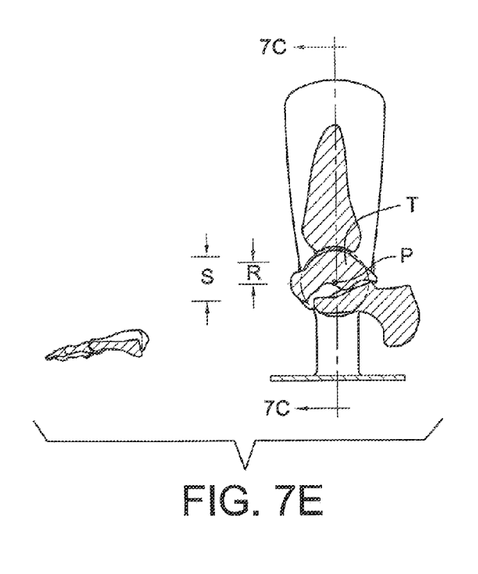
FIG. 7E is a medial side cross-sectional view of the foot and the embodiment of ankle orthosis shown in FIGS. 7A-7D, taken along line 7E-7E of FIG. 7D.

Like brace 20, as shown in FIGS. 7A, 7B and 7D, brace 50 may include a tracking guide 43 and an arcuate slot 45 associated with each hinge 58, 59. The tracking guide 43 on each side of the brace 50 may be configured to be positioned opposite (or approximately opposite) from a portion of its respective malleolus (e.g., at about the level of the tip of the medial malleolus, at the level of the tip of the medial malleolus, etc.).

Referring to FIG. 7E, placing the axes of rotation P and O of the hinges 58 and 59 of the brace 50 at about an inch below the tip of the medial malleolus, about an inch below the highest point of the tibial trochlear surface of the talus T or about an inch below the center of the talus T, provides surprising advantages. Of course, the axes of rotation P and O may be placed a variety of distances below the tibial trochlear surface of the talus T; for example, within the range S identified in FIG. 7E or within the smaller range R shown in FIG. 7E. Without limitation, the aces of rotation may be placed about 1 mm to about 35 mm beneath the tibial trochlear surface of the talus T. Such placement of the axes of rotation P and O enable movement of the foot throughout the whole range of motion between dorsiflexion and plantarflexion without little or no displacement of the tibialtalor junction (talocrural joint).

In another aspect, a brace 20, 50 of the type disclosed herein may be used to unload or stabilize the medial column of a foot, to reduce pronation principally in the mid-foot or to reduce excessive valgus position at the subtalar joint. Such a brace 20, 50 may also be used to treat grade 1 to grade 3 posterior tibial tendon dysfunction or plantas faciitis (which, in most cases is a medial compartment dysfunction).

Alternately, or in addition, a brace 20, 50 may be used to treat instability on the lateral side of the ankle and/or foot. As non-limiting examples, a brace 20, 50 may be used to unload the lateral side of the foot and/or ankle; for example, in conjunction with an ankle sprain, a peroneal sprain or after peroneal surgery.

While it is apparent that illustrative embodiments are disclosed herein, it should be appreciated that numerous modifications to and other embodiments of the disclosed subject matter may be devised by those of ordinary skill in the art. Additionally, features from any embodiment may be used in combination with features from other embodiments. The scope of each of the appended claims is limited by its plain language and the equivalents to the recited elements, not by any of the disclosed embodiments.

What is claimed:

1. An ankle brace, comprising:
   an upper member configured to be secured to a lower leg of an individual;
   a lower member configured for placement beneath at least a portion of a foot of the individual;
   a hinge connecting the upper member and the lower member, the hinge configured to be positioned at an elevation lower than a tibialtalor junction at an ankle of the individual when the upper member is secured to the lower leg of the individual; and
   a tracking element configured to stabilize the ankle during movement of a foot between full dorsiflexion and full plantarflexion, the tracking element including:
      a protruding tracking guide; and
      an arcuate receptacle for the tracking guide, the arcuate receptacle defining a path for the protruding tracking guide, the path having a shape configured to generally follow movement of a tibia of a leg of the individual over a profile of a tibial trochlea of a talus bone of the foot of the individual, the arcuate receptacle positioned at a location of the ankle brace that will substantially align the path with the tibial trochlea when the ankle brace is positioned over the ankle, the protruding tracking guide and the arcuate receptacle together defining a range of motion for the lower member.

2. The ankle brace of claim 1, wherein the hinge is configured to be positioned about an inch below an uppermost extent of the tibialtalor junction.

3. The ankle brace of claim 1, wherein the upper member includes a hinge alignment feature enabling proper positioning of the hinge.

4. The ankle brace of claim 3, wherein the hinge alignment feature comprises a recess configured to receive a malleolus of the ankle of the individual.

5. The ankle brace of claim 4, wherein the hinge alignment feature is configured to receive a medial malleolus of the ankle of the individual.

6. The ankle brace of claim 1, wherein a length of the arcuate receptacle corresponds to a normal range of motion of the foot between full dorsiflexion and full plantarflexion.

7. The ankle brace of claim 1, wherein the protruding tracking guide protrudes from the upper member at a location that corresponds to a location of a malleolus of the ankle over which the upper member is configured to be positioned.

8. The ankle brace of claim 7, wherein the location from which the protruding tracking guide protrudes from the upper member corresponds to a location of a hinge alignment element for receiving the malleolus on an opposite surface of the upper member.

9. The ankle brace of claim 7, wherein the location from which the protruding tracking guide protrudes from the upper member is opposite from an inner location of the upper member against which the malleolus is to be positioned.

10. The ankle brace of claim 1, wherein the lower member comprises an arch support.

11. The ankle brace of claim 10, wherein the arch support comprises an elongated element configured to extend downward over a medial side of the ankle, under a posterior location of a longitudinal arch of the foot of the individual and forward under the longitudinal arch.

12. The ankle brace of claim 11, wherein the arch support is configured to unload a medial column of the foot.

13. The ankle brace of claim 10, wherein the arch support is configured to substantially follow a path of a posterior tibial tendon of the foot of the individual.

14. The ankle brace of claim 13, wherein the arch support is configured to unload a medial column of the foot and to address posterior tibial tendon disorder (PTTD).

15. The ankle brace of claim 10, wherein the arch support is configured to support a longitudinal arch of the foot of the individual without requiring a ground reaction force.

16. The ankle brace of claim 15, wherein the arch support enables use of muscles and tendons of and adjacent to the longitudinal arch while walking.

17. The ankle brace of claim 16, wherein the arch support enables use of a posterior tibial tendon of the foot of the individual while walking.

18. The ankle brace of claim 1, wherein the lower member is configured to reside beneath a heel of the foot.

19. The ankle brace of claim 18, wherein the lower member is configured to reside solely beneath a posterior portion of the foot.

20. The ankle brace of claim 18, wherein the hinge comprises a pair of hinges positionable on opposite sides of the ankle.

21. The ankle brace of claim 20, wherein axes of rotation of the pair of hinges are coaxial.

* * * * *